(12) United States Patent
Jorgensen et al.

(10) Patent No.: US 6,716,187 B1
(45) Date of Patent: Apr. 6, 2004

(54) PLATELET CONCENTRATION SYRINGE KIT

(75) Inventors: Glen E. Jorgensen, Marlboro, MA (US); Bruce Berckmans, III, Palm Beach Gardens, FL (US)

(73) Assignee: Implant Innovations, Inc., Palm Beach Gardens, FL (US)

( * ) Notice: Subject to any disclaimer, the term of this patent is extended or adjusted under 35 U.S.C. 154(b) by 510 days.

(21) Appl. No.: 09/611,681

(22) Filed: Jul. 7, 2000

Related U.S. Application Data

(60) Provisional application No. 60/142,886, filed on Jul. 8, 1999.

(51) Int. Cl.[7] .............. C02F 1/38; A01N 1/02; A61K 9/70; B65D 81/00; A61M 37/00; A61M 5/315; A61M 1/36; A61B 19/00; B01L 11/00

(52) U.S. Cl. .............. 604/6.05; 494/16; 206/223; 206/571; 604/6.01; 604/6.1; 604/6.12; 604/6.15; 604/218; 604/236; 604/403; 604/407; 422/44; 422/72; 422/101; 210/782; 210/789; 435/2; 424/443; 424/532; 424/423; 600/576; 600/578

(58) Field of Search .............. 422/44, 61, 72, 422/68.1, 75, 77, 99, 101–3, 939, 940, 944; 604/4.01, 6.1, 6.01–6.05, 6.15, 6.16, 8, 9, 19, 27, 28, 30, 35–38, 500, 507, 522, 208, 218, 228, 231, 235, 236, 246, 247, 264, 272, 403, 407, 900; 210/767, 780–82, 787, 789, 800, 802, 804, 511, 513–16, 518, 542; 206/223, 568–72, 349, 363–66; 494/16, 17, 19, 20; 600/573, 576, 578–79; 435/2; 424/400, 422–26, 428, 484, 520, 443, 529, 532

(56) References Cited

U.S. PATENT DOCUMENTS

| | | | |
|---|---|---|---|
| 4,279,863 A | 7/1981 | Friehler | |
| 4,285,464 A | 8/1981 | Latham, Jr. | |
| 4,295,974 A | 10/1981 | Cornell | |
| 4,303,193 A | 12/1981 | Latham, Jr. | |
| 4,421,503 A | 12/1983 | Latham, Jr. et al. | |
| 4,425,235 A | 1/1984 | Cornell et al. | |
| 4,445,883 A | 5/1984 | Schroendorfer | |
| 4,447,220 A | 5/1984 | Eberle | 494/26 |
| 4,572,210 A * | 2/1986 | McKinnon | 600/578 |
| 4,660,569 A * | 4/1987 | Etherington | 600/578 |
| 5,000,735 A * | 3/1991 | Whelan | 604/110 |
| 5,354,483 A | 10/1994 | Furse | |
| 5,520,885 A | 5/1996 | Coelho et al. | |
| 5,585,007 A | 12/1996 | Antanavich et al. | |
| 5,707,331 A | 1/1998 | Wells et al. | |
| 5,728,040 A | 3/1998 | Schill et al. | |
| 5,788,662 A | 8/1998 | Antanavich et al. | |
| 5,858,253 A | 1/1999 | Holm | 210/702 |
| 6,063,297 A | 5/2000 | Antanavich et al. | |
| 6,086,559 A * | 7/2000 | Enk | 604/121 |
| 6,274,090 B1 * | 8/2001 | Coelho et al. | 422/101 |

FOREIGN PATENT DOCUMENTS

| | | | | |
|---|---|---|---|---|
| DE | 4445030 | * | 6/1996 | |
| DE | 44 45 030 A1 | | 6/1996 | ............. A61M/5/31 |
| DE | 197 01 263 A1 | | 7/1998 | ............. B04B/5/04 |
| EP | 0740964 A1 | | 6/1996 | |
| WO | WO 91/17778 | | 11/1991 | ............. A61M/1/36 |
| WO | WO 92/00145 | | 1/1992 | ............. B04B/5/04 |

* cited by examiner

*Primary Examiner*—Patricia Bianco
(74) *Attorney, Agent, or Firm*—Jenkens & Gilchrist

(57) ABSTRACT

A single-use system for separating blood and producing platelet concentrates includes an elongated container for receiving blood from a patient. The container has a movable plunger mounted within the blood container for expressing blood fractions separated during centrifugation of the container through a first port mounted at one end of said container, a second port mounted on the plunger, and a third port mounted on a plunger rod attached to the plunger.

5 Claims, 3 Drawing Sheets

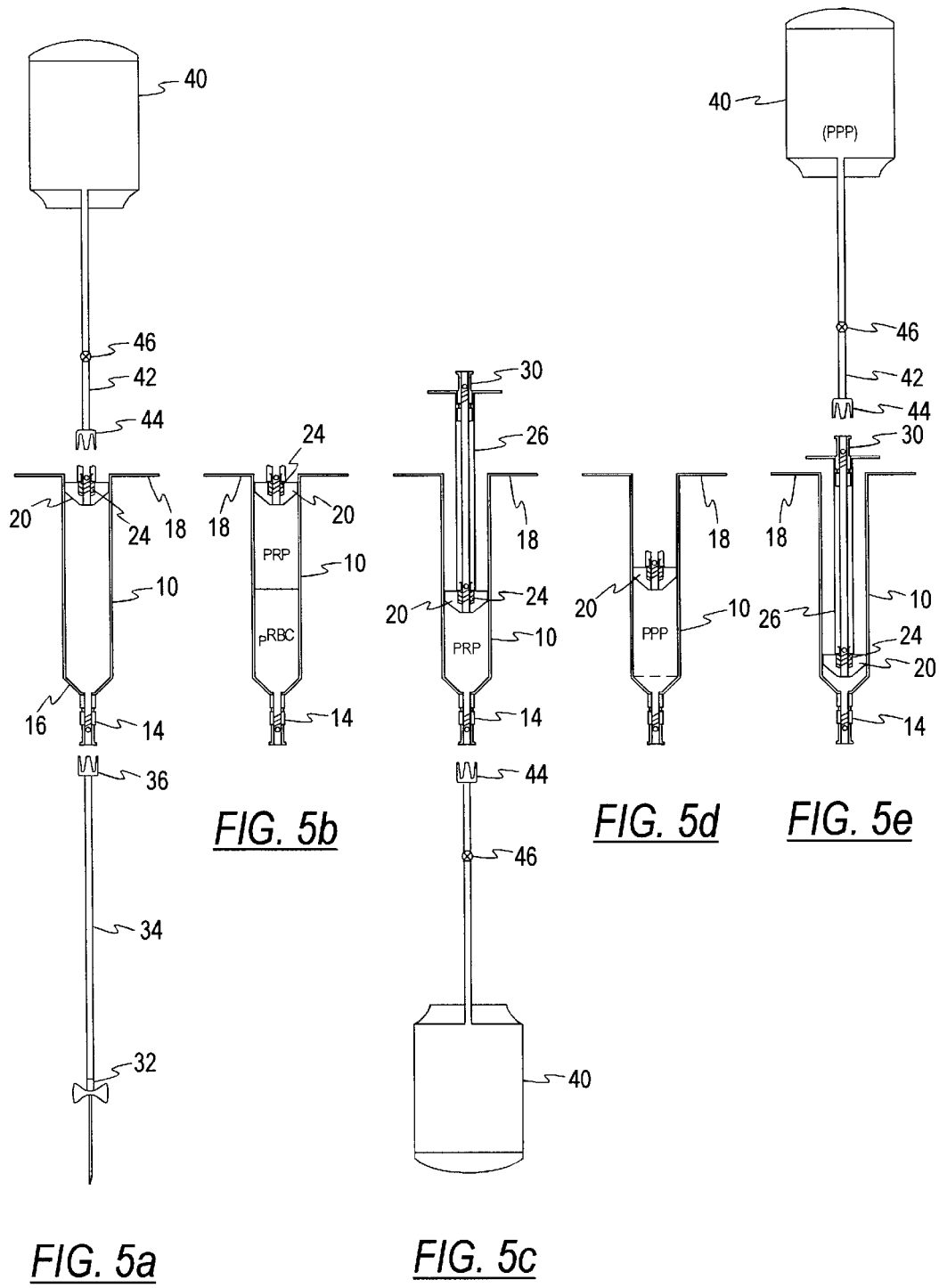

PLATELET CONCENTRATION SYRINGE KIT

This application claims the benefit of provisional application No. 60/142,886, filed Jul. 8, 1999.

FIELD OF THE INVENTION

This invention relates to processing whole blood into fractions and, more particularly, to improvements in blood processing systems for separating platelet-rich plasma from autologous blood.

BACKGROUND OF THE INVENTION

The science and effectiveness of using platelet-rich plasma derived from the patient's own blood in surgery are documented in medical, trade, and science journals. A known method for the preparation of platelets from whole blood is described in the American Association of Blood Bank's Technical Manual, 12th Edition, 1996, at pages 700–701, Method 9.11. A system employing this method collects the patient's whole blood into a collection unit with two integrally attached transfer containers. The blood is collected into the collecting container, the other two transfer containers are collapsed, and the two transfer containers with the collecting container are subjected to a "soft spin" in a centrifuge, which brings the plasma to the top of the collecting unit, leaving red cells at the bottom. In the next step, the collecting container containing the blood fractions are squeezed in a plasma extractor to force the platelet-rich plasma into one of the transfer containers through a connecting tube. A fraction comprising red cells remains behind in the collecting container, which is then removed. Next, the two transfer containers, the first being empty and the second containing the plasma, are subjected to a "heavy spin" in a centrifuge to concentrate platelets at the "bottom" of the second transfer container, leaving a platelet-poor fraction of the plasma (PPP) above the platelet concentrate (PC) in the second transfer container. The following step squeezes the second transfer container to express the PPP into the first transfer container. The platelet concentrate (PC) is then resuspended and collected for use. This system uses a process requiring six separate steps, including two centrifugal steps and two separation steps. The terms "light spin" and "heavy spin" are defined in Table 10.5-1 at page 716 of the AABB Technical Manual.

An alternative method of separating blood fractions is discussed in U.S. Pat. No. 5,102,407 and referred to as the "Amsterdam" method. Instead of two spins, soft then hard, as discussed above, a single hard spin is used in which three fractions are separated, that is, a relatively platelet-free plasma, red blood cells, and an intermediate "buffy coat" layer which contains platelets and leukocytes.

The usual procedures often employ pliable plastic bags which make it difficult to separate the blood fractions accurately. Consequently, improvements have been needed. The present invention is embodied in a new blood separation kit which provides a more convenient and efficient means for separating a patient's blood and in particular for recovering platelets.

SUMMARY OF THE INVENTION

The invention provides a single use system for separating blood and preferably for producing platelet concentrates (PC). In one embodiment, the system is in the form of a syringe kit including disposable components supplied in sterile disposable packaging, and having all of the components required to draw blood from the patient, prevent blood coagulation, separate the sample into fractions including platelet concentrate, and deliver the platelet concentrate to a surgical site. More precise separation of the separated blood fractions is possible, compared to the results achieved with pliable plastic bags. Such a system will be useful to medical and dental practitioners.

The invention may be generally described as including an elongated container, preferably cylindrical, which is adapted to be placed in a centrifuge for separating the fractions of blood introduced into the container. The container is equipped with a first port through which the blood fractions can be expelled by a plunger movably fitted within the container. The first port is located at a first end of the container and a second port is located on the movable plunger. Both ports are normally closed and they are opened from outside the container as required for removal of blood fractions. The plunger is equipped with a detachable hollow plunger rod adapted to open the second port when the plunger rod is attached to the plunger. A third port is mounted at the end of the plunger rod, the third port also is normally closed unless opened from outside the plunger rod.

In one embodiment of the invention, the container is in the form of a syringe barrel fitted with a moveable plunger. The syringe barrel is charged with a patient's blood and all of the centrifugal and separation steps are performed while the blood is in that container. The syringe barrel is adapted for use in a centrifuge, and has valves fitted at one end and within the plunger, making it possible to collect blood, centrifuge the blood in the syringe barrel, expel red blood cells after the first or soft spin, centrifuge the remaining platelet-rich plasma and expel platelet-poor plasma after the second or hard spin. The platelet concentrate remains in the syringe barrel, where it can be resuspended in a medium or media that can be introduced into the container through one of the valves.

In another embodiment, the container of the invention is given a "hard" spin, omitting the "soft" spin. Three fractions are formed, the first fraction, the red blood cells, is expelled through the first port, then the second fraction, platelet-poor plasma, is expelled through the second and third ports, leaving the third layer, consisting of platelets and plasma, for further processing.

The separation of blood fractions may be carried out manually after centrifuging the whole blood in the container. Alternatively, the separation of blood fractions could be carried out automatically in centrifuge equipment having facilities for opening the ports after it has been determined that the desired separation has been made.

Associated with the container preferably will be a needle assembly for drawing a patient's blood and which is adapted to transfer the blood into the syringe container directly or into a separate container for subsequent transfer into the syringe container. One or more waste bags adapted to receive platelet-poor plasma and red blood cells from the syringe cylinder after the soft and hard spins may be part of the syringe kit.

BRIEF DESCRIPTION OF THE DRAWINGS

FIGS. 5a through 5e show use of the syringe embodiment to prepare platelet concentrate.

DESCRIPTION OF THE ILLUSTRATIVE EMBODIMENTS

The figures illustrate a syringe embodiment of the invention adapted for manual handling in separation of blood fractions. Blood drawn from a patient is introduced into a syringe, the syringe is placed in a centrifuge and spun at the appropriate speed for a suitable period of time to cause the blood to be separated into at least two fractions. Alternatively, the separation may be automated and the blood fractions separated without manual handling of the syringe container.

Figure 1:
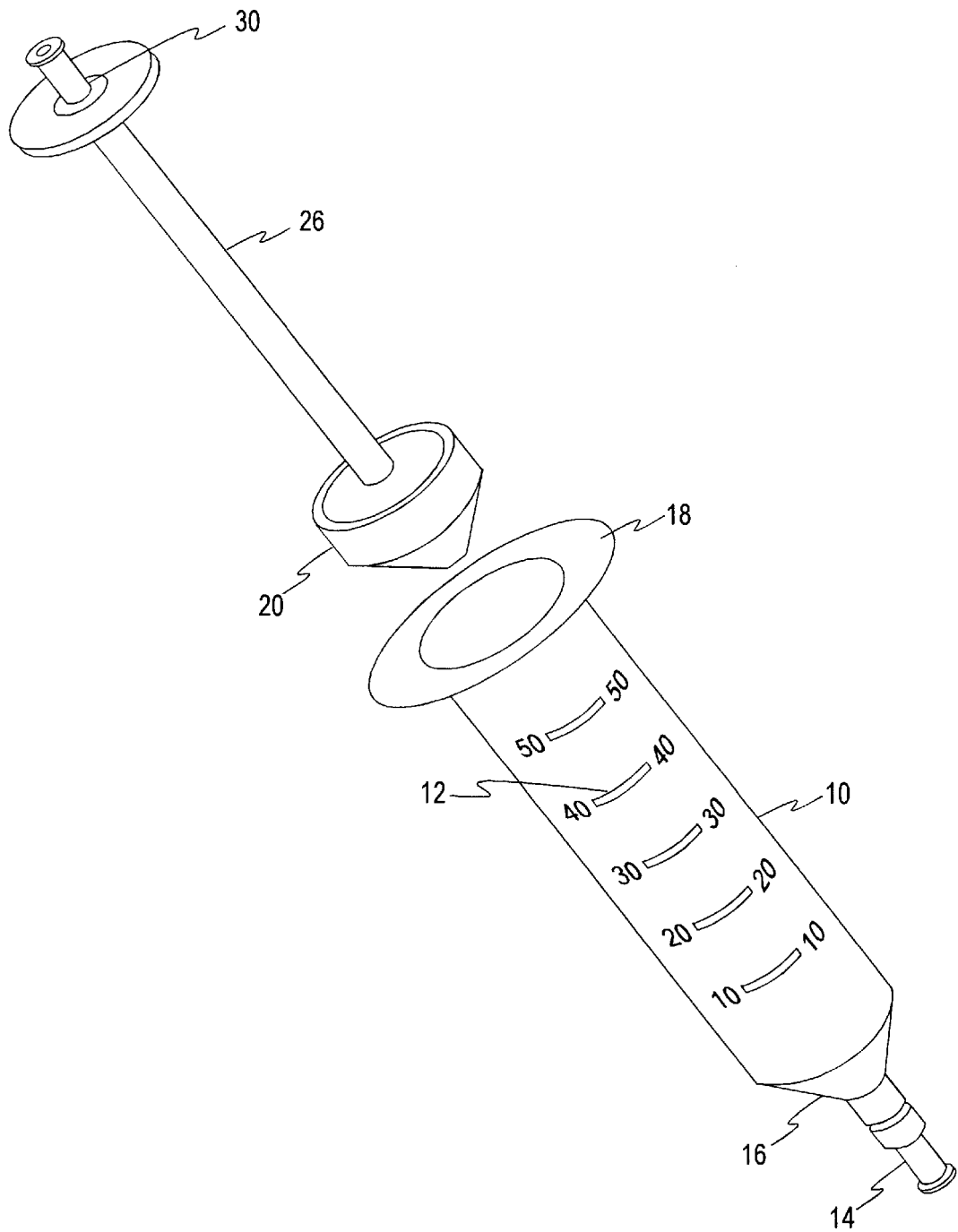
FIG. 1 is an isometric view of a elongated syringe container and associated components.
Figures 2, 3, 4:
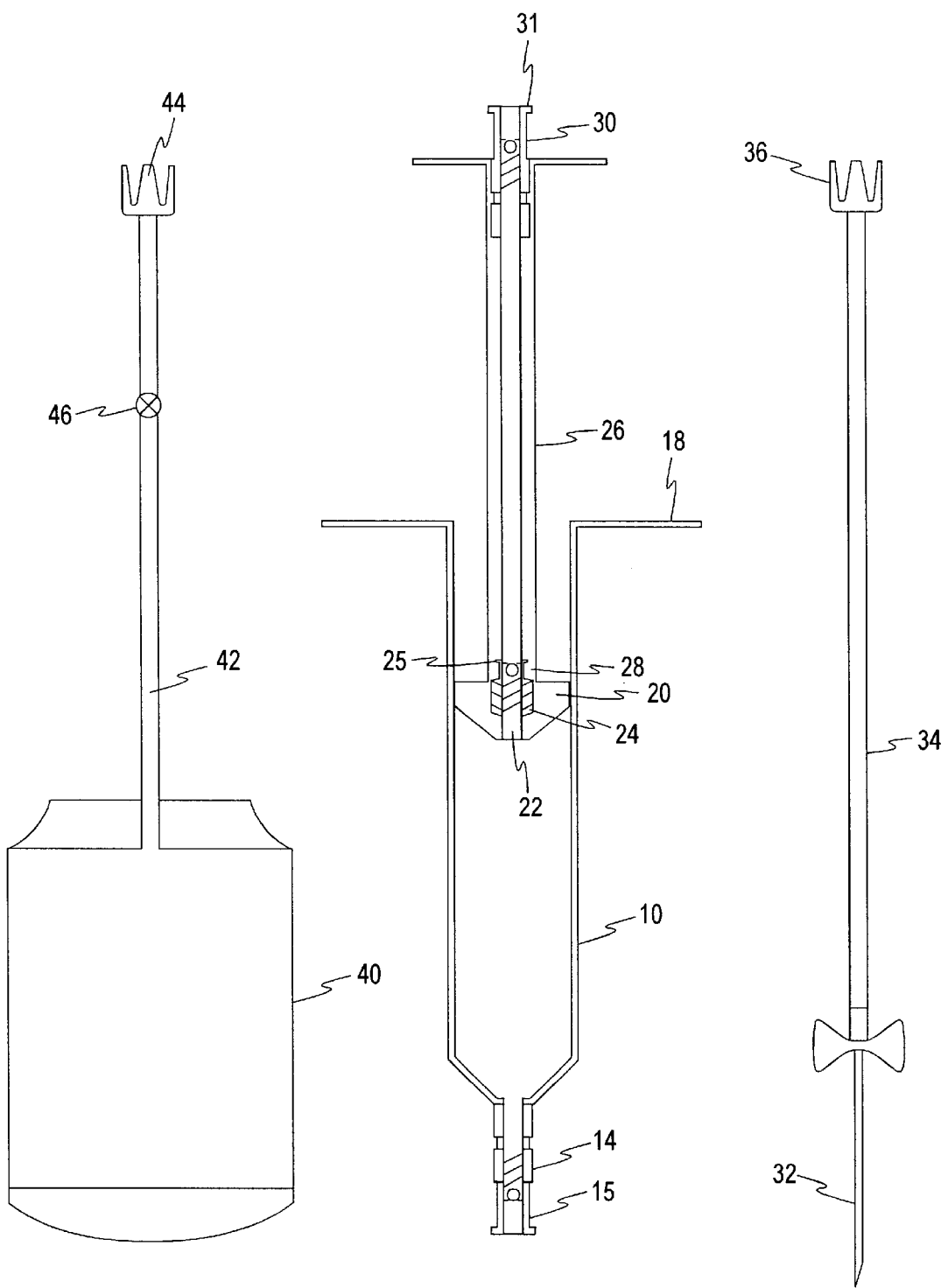
FIG. 2 is a longitudinal section through FIG. 1.
FIG. 3 shows a blood-collector needle.
FIG. 4 shows a waste bag.

FIG. 1 shows an elongated container 10, bearing graduated marks 12 to indicate the volume of its contents (not shown). The container has a first port, shown in the drawing as including a spring-loaded ball seat valve 14, at a first end 16 and a radially-extending flange 18 at its other end. A plunger 20 fits slidably within the container and prevents blood from passing between the wall of the container and the plunger. The plunger has a through passage 22 fitted as a second port, also shown as a spring-loaded ball seat valve 24 (FIG. 2). The valve 24 could be omitted if desired, in which case, it would be necessary to temporarily seal the opening while the container is being centrifuged to separate the blood fractions. A tubular plunger rod 26 is adapted at one end 28 to engage the spring-loaded ball seat valve 24. The plunger rod has another spring-loaded ball seat valve 30 at its other end remote from the plunger. The valves 14, 24 and 30 may have a "Luer" fitting, which has a coupling 15, 25 and 31, respectively, for removably connecting to another article (for example, a hose). This type of valve is normally closed when nothing is connected to its coupling, and the valve can be opened when the protruding feature of a mating connector forces the ball away from the valve seat. It should be understood that the valves need not be the spring-loaded ball seat valves shown in the drawings, but may be other types capable of preventing the escape of the blood components and of being opened when needed, for example a valve in which a silicone plunger seals against a conical valve seat, the compression of which closes the valve until activated. More broadly, the ports may include other means for blocking flow of the blood components rather than the valves in the figures.

The container 10 and associated parts of the kit, particularly the plunger 20 and plunger rod 26, differ from conventional pliable plastic bags in being made of relatively stiff materials, for example polycarbonate, polypropylene, ABS or equivalents. It is an advantage of the present invention that, since the container walls are relatively rigid, the problems associated with separating blood fractions in a pliable bag are avoided. Moving the plunger within the container creates minimal disturbance of the separated blood layers, thereby enabling a more precise separation to be made.

FIG. 3 shows a needle 32 for taking blood from a patient connected to one end of a tube 34 which has at its other end a fitting 36 that is adapted to connect to any of the couplings 15, 25 or 31. Thus, blood may be introduced directly into container 10 through valve 14 or alternatively, blood may be directed to a separate bag for subsequent transfer into the container for separation.

FIG. 4 shows a waste bag 40, typically but not necessarily a pliable plastic bag, connected to one end of a tube 42 which has at its other end a fitting 44 that is adapted to connect to any of the couplings 15, 25 or 31, thereby opening the associated valve. The tube 42 is fitted with a tubing clamp 46. The container 10 and associated parts shown in FIGS. 1–4, inclusive, comprise the syringe kit of this embodiment of the invention. The container 10, shorn of associated parts (plunger rod 26, needle 32 and tube 34, and waste bag 40 and tube 42) may be adapted for fitting in a centrifuge bucket (not shown) and used to separate blood into its fractions and to prepare platelet concentrate, as is described with reference to FIGS. 5a–5e, inclusive.

In FIG. 5a, the plunger 20 is at the top of the container 10, near the flange 18, the needle 32 is connected to check valve 14, which is held open, the waste bag 40 is connected to the plunger check valve 24 holding that valve open, and the clamp 46 is open. The container may be empty or it may contain a small amount of a blood anti-coagulant. When the needle 32 draws blood from a patient, the blood flows into the container under pressure from the patient, displacing air from the container 10, which air is received in the waste bag 40. When the container 10 is charged with blood, the waste bag 40 and needle 32 are decoupled from the valves 14 and 24, which are closed by the associated springs. Alternatively, the waste bag 40 is not used and instead, the plunger 20 may be used to extract blood directly from the patient in a manner similar to a conventional syringe. The container is subjected to a light spin in a centrifuge (not shown). As is shown in FIG. 5b, this step separates red blood cells (PRBC) from platelet-rich plasma (PRP). In the next step, shown in FIG. 5c, the waste bag is connected to valve 14, and the plunger rod 26 is connected to the plunger via the valve 24. The valves 14 and 24 and the waste bag clamp 46 are all open, but the valve 30 at the free end of the plunger rod is closed. The plunger rod 26 is used to push the plunger into the container, expelling the red blood cells into the waste bag 40. The container now contains primarily platelet-rich plasma. The clamp 46 is closed, and the plunger rod and the waste bag 40 are decoupled from the container, thus closing valves 14 and 24.

The container 10, shorn of the bag and plunger rod, as shown in FIG. 5d, is next subjected to a hard spin, which concentrates platelets at the bottom end 16 of the container 10, leaving platelet-poor plasma (PPP) above the platelet concentrate. The final step in the process, that of removing the platelet-poor plasma from the container, is illustrated in FIG. 5e. The plunger rod 26 is again attached to the plunger 20, and the waste bag 40 is coupled to the free end of the plunger rod through the valve 30. The valves 24 and 30 and the clamp 46 are all open, and the valve 14 is closed. The plunger is driven toward the lower end 16 of the container, and the platelet-poor plasma is forced through the passageway in plunger rod 26 and the tube 44 into the waste bag. The clamp 46 is then closed, and the waste bag 40 and, if desired, the plunger rod 26 may be removed from the container. With the waste bag removed, the plunger rod valve 30 will close, so failure to remove the plunger rod will not affect the contents of the container. The container 10 is now left with the platelet concentrate in it.

The above description covers a simple manual operation in which the syringe kit is used in a particular manner to separate blood into three fractions by successive soft and hard spins. It is also feasible to use only one "hard" spin to separate the blood in a single step into three fractions (i.e., red blood cells, plasma and an intermediate layer containing platelets). The three fractions can be separated by expelling both the plasma and red blood cells separately or simultaneously, leaving the intermediate layer for further processing. Alternatively, such manual operations can be automated.

It should be understood that the syringe kit described above is a preferred embodiment, but that modifications may be made without departing from the scope of the invention as defined by the following claims.

What is claimed is:

1. A blood separation kit comprising:
   (a) an elongated hollow container having a first end and a second end and comprising a first port mounted at said first end for admitting liquid to or expelling liquid from said container, said port being closed unless opened by a fitting attached to said port;
   (b) a plunger movably disposed within and engaging the walls of said container of (a), said plunger comprising
      (1) a passageway through said plunger communicating with the interior of said container of (a), and
      (2) a second port for expelling liquid mounted within said passageway of (b)(1), said port being closed unless opened by a fitting attached to said port; and
   (c) a plunger rod having a passageway therein and adapted to engage said plunger of (b), said plunger rod comprising
      (1) means for engaging said plunger to provide communication with the inside of the container of (a) via the passageway in the plunger of (b) to the passageway in said plunger rod,
      (2) a third port for expelling liquid mounted at the end of said plunger rod opposite said means for engaging said plunger, said third port being closed unless opened by a fitting attached to said third port.

2. A blood separation kit of claim 1, further comprising:
   (d) a needle set comprising:
      (1) a hollow needle for taking a sample of a patient's blood;
      (2) a hollow tube attached to and communicating with said needle for transferring said patients blood to the container of (a); and
      (3) a fitting adapted to engage the first port of (a) and to open said first port.

3. A blood separation kit of claim 1, further comprising:
   (e) a waste bag having a hollow tube connected to and communicating with the interior of said bag for receiving separated blood fractions;
   (f) a fitting adapted to engage the first and third ports (a) and (c)(2) respectively and to open said first and third ports; and
   (g) a clamp mounted on the tube of (e) for opening and closing the hollow tube of (e).

4. A blood separation kit of claim 1, wherein said first, second, and third ports comprise valves positioned to prevent expelling blood fractions during centrifugation of blood in said container.

5. A blood separation kit comprising:
   (a) an elongated hollow container having a first end and a second end and comprising a first port mounted at said first end for admitting liquid to or expelling liquid from said container, said port being closed unless opened by a fitting attached to said port;
   (b) a plunger movably disposed within and engaging the walls of said container of (a), said plunger comprising
      (1) a passageway through said plunger communicating with the interior of said container of (a), and
      (2) a second port for expelling liquid mounted within said passageway of (b)(1), said port being closed unless opened by a fitting attached to said port; and
   (c) a plunger rod having a passageway therein and adapted to engage said plunger of (b), said plunger rod comprising
      (1) means for engaging said plunger to provide communication with the inside of the container of (a) via the passageway in the plunger of (b) to the passageway in said plunger rod,
      (2) a third port for expelling liquid mounted at the end of said plunger rod opposite said means for engaging said plunger, said third port being closed unless opened by a fitting attached to said third port;
   (d) a needle set comprising:
      (1) a hollow needle for taking a sample of a patients blood;
      (2) a hollow tube attached to and communicating with said needle for transferring said patients blood to the container of (a);
      (3) a fitting adapted to engage the first port of (a) and to open said first port;
   (e) a waste bag having a hollow tube connected to and communicating with the interior of said bag for receiving separated blood fractions;
   (f) a fitting adapted to engage the first and third ports (a) and (c)(2) respectively and to open said first and third ports; and
   (g) a clamp mounted on the tube of (e) for opening and closing the hollow tube of (e).

* * * * *